US011111742B2

(12) United States Patent
Amanullah et al.

(10) Patent No.: US 11,111,742 B2
(45) Date of Patent: Sep. 7, 2021

(54) APPARATUS FOR LOSS CIRCULATION MATERIAL PERFORMANCE EVALUATION

(71) Applicant: Saudi Arabian Oil Company, Dhahran (SA)

(72) Inventors: Md Amanullah, Dhahran (SA); Jothibasu Ramasamy, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 869 days.

(21) Appl. No.: 15/879,783

(22) Filed: Jan. 25, 2018

(65) Prior Publication Data

US 2018/0266197 A1    Sep. 20, 2018

Related U.S. Application Data

(60) Provisional application No. 62/472,353, filed on Mar. 16, 2017.

(51) Int. Cl.
*E21B 21/00* (2006.01)
*G01N 15/08* (2006.01)
(Continued)

(52) U.S. Cl.
CPC .............. *E21B 21/003* (2013.01); *C09K 8/80* (2013.01); *E21B 43/267* (2013.01); *E21B 49/08* (2013.01);
(Continued)

(58) Field of Classification Search
CPC ........ C09K 8/80; E21B 21/003; G01N 15/082
See application file for complete search history.

(56) References Cited

U.S. PATENT DOCUMENTS 2,646,678 A * 7/1953 Standing ............... B01D 29/111
 210/455
2,733,595 A * 2/1956 Twining ................ E21B 21/003
 73/38
(Continued)

FOREIGN PATENT DOCUMENTS

WO    2009029451    3/2009
WO    2010064009    6/2010
(Continued)

OTHER PUBLICATIONS

International Search Report and Written Opinion issued in International Application No. PCT/US2019/054408 dated Feb. 21, 2020, 18 pages.

(Continued)

*Primary Examiner* — John Fitzgerald
(74) *Attorney, Agent, or Firm* — Fish & Richardson P.C.

(57) ABSTRACT

An apparatus for evaluating loss circulation material (LCM) in loss circulation zones is described. The apparatus includes a drilling fluid reservoir that can carry a wellbore drilling fluid. The apparatus includes a LCM reservoir that can carry a LCM. The apparatus includes a spacer fluid reservoir that can carry a spacer fluid. The apparatus includes a LCM test cell that includes a disk member that includes multiple openings. The disk member represents a loss circulation zone in a subterranean zone in which a wellbore is drilled using the wellbore drilling fluid. The LCM test cell is fluidically connected to the drilling fluid reservoir, the LCM reservoir and the spacer fluid reservoir. The LCM test cell is configured to fluidically receive a quantity of LCM from the LCM reservoir and to evaluate an ability of the LCM to decrease loss circulation through the loss circulation zone.

17 Claims, 5 Drawing Sheets

(51) Int. Cl.
*E21B 49/08* (2006.01)
*C09K 8/80* (2006.01)
*E21B 43/267* (2006.01)
*G01N 33/28* (2006.01)
*G01N 11/04* (2006.01)

(52) U.S. Cl.
CPC .......... *G01N 11/04* (2013.01); *G01N 15/082* (2013.01); *G01N 33/2823* (2013.01)

(56) References Cited

U.S. PATENT DOCUMENTS

| | | | |
|---|---|---|---|
| 5,161,407 A | 11/1992 | Ankeny et al. | |
| 6,055,850 A | 5/2000 | Turner et al. | |
| 7,900,504 B2* | 3/2011 | Huynh | G01N 33/2823 73/61.41 |
| 8,151,633 B2* | 4/2012 | Jamison | E21B 21/003 73/54.14 |
| 8,863,567 B2* | 10/2014 | Jappy | E21B 21/003 73/61.64 |
| 8,972,235 B2* | 3/2015 | Murphy | G01N 33/24 703/10 |
| 9,285,355 B2* | 3/2016 | Murphy | E21B 49/008 |
| 9,714,565 B2* | 7/2017 | Blue | G01N 33/2823 |
| 10,041,871 B2* | 8/2018 | Jamison | G01N 11/04 |
| 10,180,063 B2* | 1/2019 | Murphy | E21B 49/008 |
| 10,584,582 B2* | 3/2020 | Murphy | E21B 49/008 |
| 2008/0236891 A1* | 10/2008 | Huynh | G01N 15/08 175/48 |
| 2010/0032031 A1* | 2/2010 | Neal | E21B 21/02 137/565.01 |
| 2010/0139387 A1* | 6/2010 | Jamison | E21B 21/003 73/152.25 |
| 2011/0120217 A1* | 5/2011 | Huynh | E21B 21/08 73/152.22 |
| 2011/0290012 A1 | 12/2011 | Jappy et al. | |
| 2012/0152000 A1* | 6/2012 | Jamison | G01N 33/2823 73/54.14 |
| 2013/0192358 A1* | 8/2013 | Murphy | E21B 49/008 73/152.05 |
| 2013/0218545 A1* | 8/2013 | Murphy | E21B 43/26 703/10 |
| 2013/0298662 A1* | 11/2013 | Jamison | G01N 11/04 73/152.18 |
| 2014/0102188 A1 | 4/2014 | Murphy et al. | |
| 2014/0182369 A1* | 7/2014 | Blue | G01N 33/2823 73/152.27 |
| 2014/0216149 A1 | 8/2014 | Zhou et al. | |
| 2016/0033382 A1* | 2/2016 | Jamison | G01N 11/04 73/152.18 |
| 2016/0061701 A1 | 3/2016 | Amanullah et al. | |
| 2016/0130939 A1* | 5/2016 | Murphy | G01N 33/2823 73/152.05 |
| 2018/0266197 A1 | 9/2018 | Amanullah et al. | |
| 2019/0112922 A1* | 4/2019 | Murphy | E21B 49/008 |
| 2020/0110014 A1* | 4/2020 | Amanullah | G01N 11/02 |
| 2020/0110015 A1* | 4/2020 | Amanullah | G01N 15/0826 |
| 2020/0370431 A1* | 11/2020 | Amanullah | E21B 49/087 |

FOREIGN PATENT DOCUMENTS

| | | |
|---|---|---|
| WO | 2013126287 | 8/2013 |
| WO | 2018005575 | 1/2018 |

OTHER PUBLICATIONS

Hettema et al., ""Development of an Innovative High-Pressure Testing Device for the Evaluation of Drilling Fluid Systems and Drilling Fluid Additives Within Fractured Permeable Zone,"" Retrieved from the Internet: URL: <https://www.onepetro.org/download/conference-paper/OMC-2007-082? i d=conference-paper/OMC-2007-082>, Offshore Mediterranean Conference and Exhibition, Mar. 28-30, 2007, 14 pages.

Fann, "Permeability Plugging Apparatus (PPA)," XP055060626, Fann product information, Drilling Fluids, Jan. 1, 2007, 2 pages.

International Search Report and Written Opinion issued in International Application No. PCT/US2018/022229 dated Jul. 6, 2018, 15 pages.

Smith and Growcock, "AADE-11-DF-HO-24 Wellbore Strengthening While Drilling Above and Below Salt in the Gulf of Mexico," presented at the 2008 AADE Fluids Conference and Exhibition on Apr. 8-9, 2008, 6 pages.

Whitfill and Miller, "AADE-08-NTCE-21 Developing and Testing Lost Circulation Materials," presented at the 2008 AADE Fluids Conference and Exhibition on Apr. 8-9, 2008, 11 pages.

Miller et al., "Laboratory apparatus improves simulation of lost circulation conditions," AADE-13-FTCE-09, AADE, American Association of Drilling Engineers, presented at the 2013 AADE National Technical Conference and Exhibition, Feb. 26-27, 2013, 8 pages.

Gulf Cooperation Council Examination Report issued in GCC Application No. GC 2018-34953 dated Oct. 8, 2019, 4 pages.

GCC Examination Report in Gulf Cooperation Council Appln. No. GC 2018-34953, dated Jan. 27, 2021, 3 pages.

GCC Examination Report in Gulf Cooperation Council Appln. No. GC 2019-38407, dated Oct. 30, 2020, 5 pages.

* cited by examiner

FIG. 2A
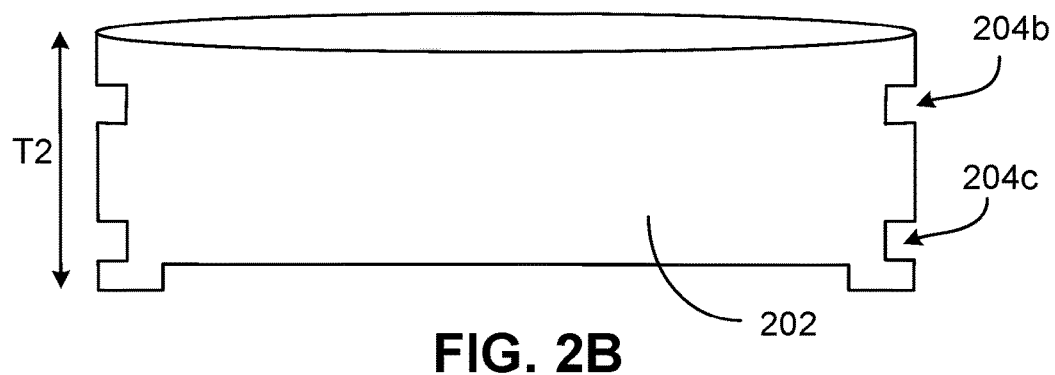
FIG. 2B
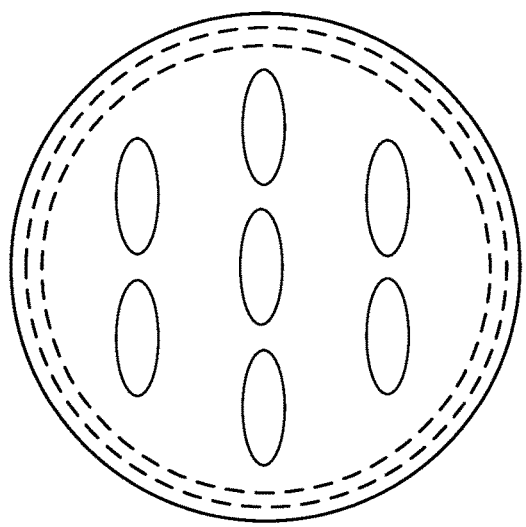        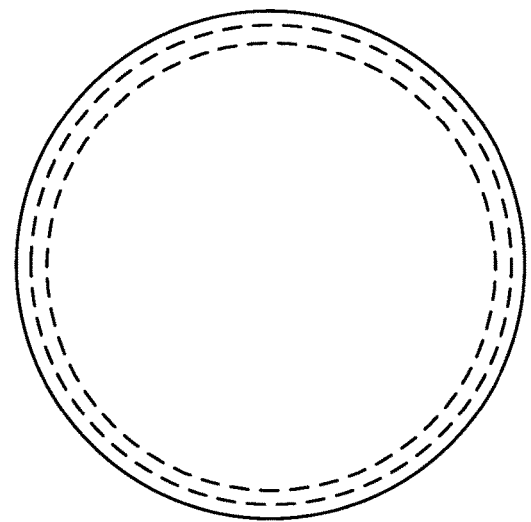
FIG. 2C                         FIG. 2D

APPARATUS FOR LOSS CIRCULATION MATERIAL PERFORMANCE EVALUATION

CROSS-REFERENCE TO RELATED APPLICATION

This application claims the benefit of priority to U.S. Provisional Patent Application Ser. No. 62/472,353, filed Mar. 16, 2017, the contents of which are hereby incorporated by reference.

TECHNICAL FIELD

This disclosure relates to testing apparatus, for example, apparatus to test fluid flow into the formation of a wellbore.

BACKGROUND

In wellbore drilling, a drilling fluid (or drilling mud) is circulated from a surface of the wellbore to downhole through the drill string. The fluid exits through ports (or jets) in the drill bit, picking up cuttings and carrying the cuttings up an annulus formed between an inner wall of the wellbore and an outer wall of the drill string. The fluid and the cuttings flow through the annulus to the surface, where the cuttings are separated from the fluid. The fluid can be treated with chemicals and then pumped into the wellbore through the drill string to repeat the process.

Lost circulation is a situation in which the flow of the drilling fluid up the annulus toward the surface is reduced or is totally absent. For example, lost circulation results because a portion of the subterranean zone encountered while drilling has a permeability, openings, flow channels, fractures, vugs and/or caves that causes all or a portion of the drilling fluid to be lost into these loss zones. Lost circulation can be countered by introducing loss circulation material (LCM) into the wellbore. The LCM reduces the permeability or fluid flow capability totally or partially of the portion of the subterranean zone minimizing or preventing loss of the drilling fluid into the portion.

SUMMARY

This specification describes technologies relating to LCM performance evaluation. This specification also describes a test apparatus to test and evaluate the performance of LCM.

Certain aspects of the subject matter described here can be implemented as a LCM testing apparatus. The apparatus includes a drilling fluid reservoir that can carry a wellbore drilling fluid. The apparatus includes a LCM reservoir that can carry a LCM. The apparatus includes a spacer fluid reservoir that can carry a spacer fluid. The apparatus includes a LCM test cell that includes various disk members that includes multiple openings of various sizes to simulate loss zone of various nature such as seepage, moderate and severe. The disk member represents a loss circulation zone in a subterranean zone in which a wellbore is drilled using the wellbore drilling fluid. The LCM test cell is fluidically connected to the drilling fluid reservoir, the LCM reservoir and the spacer fluid reservoir. The LCM test cell is configured to fluidically receive a quantity of LCM from the LCM reservoir and to evaluate an ability of the LCM to stop or decrease loss circulation through the loss circulation zone.

This, and other aspects, can include one or more of the following features. The apparatus can include a fluid transfer network, which can include four elongate tubular members. A first elongate tubular member can be fluidically coupled to the LCM test cell. A second elongate tubular member can be fluidically coupled to the drilling fluid reservoir and to the first elongate tubular member. A third elongate tubular member can be fluidically coupled to the drilling fluid reservoir and to the first elongate tubular member. A fourth elongate tubular member can be fluidically coupled to the spacer fluid reservoir and to the first elongate tubular member. The fluid transfer network can flow at least one of the wellbore drilling fluid, the LCM or the spacer fluid to the LCM test cell.

With or without any of the other aspects, the LCM test cell can be configured to evaluate a sealing efficiency of the LCM. The sealing efficiency is an ability of the LCM to prevent flow of wellbore drilling fluid through the plurality of openings in the disk member. The spacer fluid is incorporated in some cases to prevent the contamination of wellbore drilling fluid due to the mixing effect of LCM pill or loss control slurry with the drilling mud.

With or without any of the other aspects, each of the drilling fluid reservoir, the LCM reservoir, the spacer fluid reservoir and the LCM test cell can include a respective nitrogen pressure inlet configured to receive nitrogen and to transfer the received nitrogen to the LCM test cell to apply a pressure on a mixture of the wellbore drilling fluid and the spacer fluid including the quantity of the LCM to evaluate the ability of the LCM to decrease loss circulation through the simulated loss circulation zone.

With or without any of the other aspects, the apparatus can include a valve network, which can include four valves. A first valve can be in a flow path through the first elongate tubular member. A second valve can be in a flow path through the second elongate tubular member. A third valve can be in a flow path through the third elongate tubular member. A fourth valve can be in a flow path through the fourth elongate tubular member. The valve network can selectively flow at least one of the wellbore drilling fluid, the LCM or the spacer fluid to the LCM test cell.

With or without any of the other aspects, the apparatus can include a first base member supporting the drilling fluid reservoir, the LCM reservoir and the spacer fluid reservoir, and a second base member supporting the LCM test cell. The second base member can be positioned vertically lower than the first base member relative to a floor on which the first base member and the second base member are positioned, the floor being below the first base member and the second base member.

With or without any of the other aspects, the LCM test cell can include an inlet fluidically connected to the first elongate tubular member and an outlet. A LCM test cell region between the inlet and the outlet can define a fluid flow path. The disk member can be positioned within the flow path such that fluid flowed from the inlet to the outlet at least partially flows through the disk member.

With or without any of the other aspects, the LCM test cell can be pressurized up to 2000 pounds per square inch (psi).

With or without any of the other aspects, each of the drilling fluid reservoir, the spacer fluid reservoir and the LCM reservoir can be pressurized up to 500 psi.

With or without any of the other aspects, the disk member including the multiple openings can be a first disk member that includes multiple openings of various sizes, each of which is substantially up to 40 millimeter (mm) in size.

With or without any of the other aspects, the apparatus can include multiple disk members, each including multiple openings. A second of the multiple disk members can include openings ranging between substantially 5 mm and up to 40 mm in size.

Certain aspects of the subject matter described here can be implemented as a method of evaluating a LCM. Wellbore drilling fluid is stored in a drilling fluid reservoir. LCM is stored in a LCM reservoir. Spacer fluid is stored in a spacer fluid reservoir. The LCM test material is flowed to a LCM test cell fluidically coupled to the drilling fluid reservoir, the LCM reservoir and the spacer fluid reservoir. The LCM test material includes a quantity of LCM from the LCM reservoir. The LCM test material is pressurized to flow through a disk member including multiple openings. The disk member is positioned within the LCM test cell and represents a loss circulation zone in a subterranean zone in which a wellbore is drilled using the wellbore drilling fluid. An ability of the LCM to decrease loss circulation through the loss circulation zone is evaluated based on the flow of at least a portion of the LCM test material through the disk member.

This, and other aspects, can include one or more of the following features. To pressurize the LCM test material to flow through the disk member including the multiple openings, the disk member can be placed to the LCM test cell between an inlet to the LCM test cell and an outlet to the LCM test cell. A quantity of the LCM test material that flows from the inlet through the disk member through the outlet within a certain duration can be measured.

With or without any of the other aspects, to pressurize the LCM test material, a nitrogen pressure can be applied to pressurize the LCM test cell to flow the LCM test material toward the loss simulating disk member in the LCM test cell.

With or without any of the other aspects, to evaluate the ability of the LCM, a sealing efficiency of the LCM can be determined. The sealing efficiency is an ability of the LCM to prevent flow of a mixture of the wellbore drilling fluid through the plurality of openings in the disk member. The spacer fluid is sometimes used to prevent contamination of wellbore fluid due to the mingling action of the LCM slurry and the wellbore fluid at the interface.

With or without any of the other aspects, to flow the LCM test material to the LCM test cell, the drilling fluid reservoir, the LCM reservoir and the spacer fluid reservoir can be positioned on a first base member. The LCM test cell can be positioned on a second base member positioned vertically lower than the first base member relative to a floor on which the first base member and the second base member are positioned, the floor being below the first base member and the second base member. The LCM test material flows to the LCM test cell under gravity or under the action of an applied pressure if the LCM slurry is unable to flow under the action of gravity force.

With or without any of the other aspects, a first quantity of the drilling fluid or a second quantity of the spacer fluid or a third quantity of the LCM flowed to the LCM test cell can be controlled using a fluid transfer network that fluidically couples the drilling fluid reservoir, the spacer fluid reservoir and the LCM reservoir, and a valve network that controls flow of the drilling fluid, the spacer fluid and the LCM to the LCM test cell.

With or without any of the other aspects, the LCM test material can be pressurized to a pressure of substantially 2000 psi.

With or without any of the other aspects, the LCM test material can be flowed to the LCM test cell at a pressure of substantially 500 psi.

The details of one or more implementations of the subject matter described in this specification are set forth in the accompanying drawings and the description later. Other features, aspects, and advantages of the subject matter will become apparent from the description, the drawings, and the claims.

BRIEF DESCRIPTION OF THE DRAWINGS

FIGS. 2A-2D are schematic diagrams of disk members, each with multiple openings.

Like reference numbers and designations in the various drawings indicate like elements.

DETAILED DESCRIPTION

Figure 1:
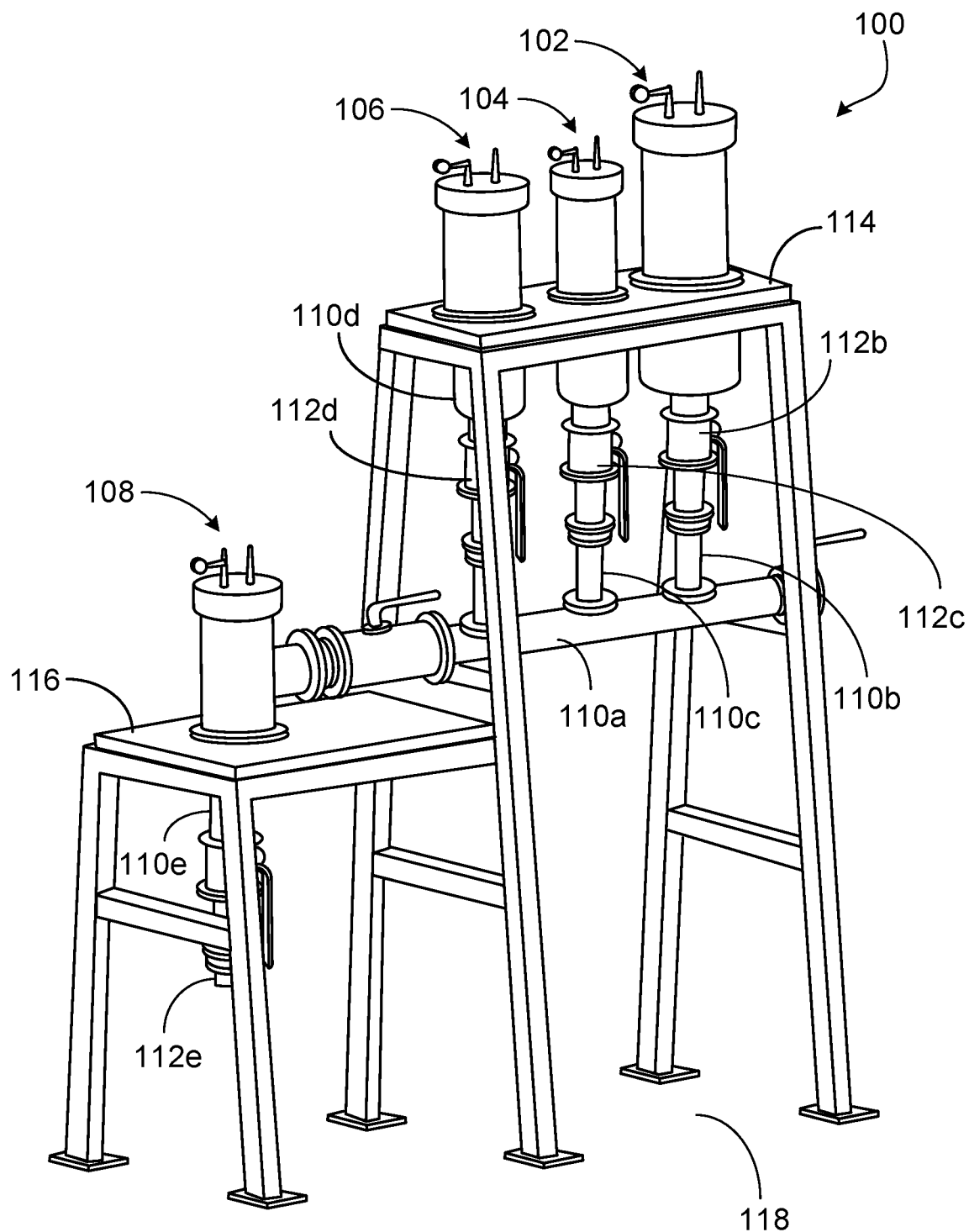
FIG. 1 is a schematic drawing of an example LCM test apparatus.

Lost circulation contributes to drilling non-productive time. Loss of circulation while drilling can range from seepage (low loss) to moderate or severe losses. When encountering a high-permeability, super-k, fractured, vugular or cavernous formation while drilling, a large volume of drilling mud can be lost into the formation with a quick drop of mud column in the wellbore. The drop of mud column can trigger drilling problems such as stuck pipe, wellbore instability, kick or blowout leading to side tracking or abandonment of a well. Addressing lost circulation along with the problems triggered by a loss circulation event can be expensive (for example, in the range of millions of dollars annually), with a portion of the costs being directed to the procurement of various LCMs to treat the seepage, moderate or severe loss zones.

LCMs are specifically designed to combat lost circulation. The design and development of LCMs involves performance evaluation using pore plugging tests performed in laboratories. A pore plugging test can be used to evaluate materials for seepage (that is, low losses) to moderate losses. In the pore plugging test, disks having openings (for example, slots) of different sizes (for example, 0.5 mm, 1 mm, 2 mm or a different size) are used to evaluate the LCM under given temperature and pressure conditions by flowing a mixture of the LCM and drilling fluid through the disks. The sizes of the openings correspond to the sizes of the fractures in the loss circulation zone in the subterranean zone. A pore plugging test using disks of the sizes described earlier are often insufficient to evaluate LCMs designed for severe loss zones because the sizes of the openings in the severe loss zones are greater than those in the seepage or moderate-type zones, rendering the disks described earlier ineffective or unsuitable.

This disclosure describes a design, development and method of use of a test apparatus for LCM performance evaluation, for example, for LCM designed for use in severe loss zones. The types of LCM that can be evaluated can include, for example, particulate type LCM, flake type LCM, fibrous LCM, various combination of particulate, flaky and fibrous LCMs, two component systems, rapid squeeze type LCMs, shaped LCMs, and the like. The evaluated LCM can be used in any type of loss circulation application, for example, severe or total loss of circulation. As described later, the test apparatus includes multiple components, for example, a test cell, a mud reservoir, a spacer or activator reservoir and a LCM reservoir. The components are engineered and assembled in a systematic way using various fixtures, for example, ball valves, relief valves, connecting pipes, pressure inlets, fluid outlets, disks with slotted and openings or holes (non-circular or circular in cross-section) to simulate various loss zones, and associated components. The test cell is configured to hold one or more of several disks, for example, metal disks with openings that represent a loss zone. In general, the disks can be made of materials that are resistant to the pressures within the reservoirs described later and chemically resistant to the fluids flowed through the disks. The openings can be slots (for example, up 40 mm in size) that represent a fractured loss zone or circular holes that represent vugular loss zones. In some implementations, the slots can be circular holes. Alternatively, or in addition, the slots can be non-circular. The diameters of the circular openings or the widths of the non-circular slots on the same disk can be the same or different.

As described later, the test apparatus can be used to test various LCM products up to a threshold working pressure (for example, up to 2000 pounds per square inch (psi)). The reservoir chambers, each of which includes the drilling fluid, spacer and LCM slurry, respectively, are individually connected to the test cell using fluid lines that can flow the respective fluid to the test cell at a flow pressure (for example, up to 500 psi). After flowing the desired material (for example, the LCM slurry and at least one of the drilling fluid or the spacer), the test cell can be sealed and the reservoirs can be closed. The test cell can then be pressurized for a duration (for example, 30 minutes or similar duration) by applying a working pressure up to or less than the threshold working pressure. The pressure causes the material in the test cell to flow through the disks in the test cell toward an outlet of the test cell. A quantity of material that flows out of the test cell within the test duration is collected to evaluate the performance of the LCM. After completing the test, the pressure from the test cell is released, the left over material is removed and the test apparatus is cleaned to prepare for a subsequent test.

Implementations of the subject matter disclosed in this specification can enable constructing a test apparatus for evaluation of LCM for extreme drilling conditions applicable in a loss circulation zone having vugs or large fractures (or both). Implementations can also enable testing the LCM. Implementations can also allow determining a suitability of a LCM to prevent or minimize lost circulation in severe loss zones, moderate loss zones or seepage zones.

FIG. 1 is a schematic drawing of an example LCM test apparatus 100. The apparatus 100 can be implemented to evaluate effectiveness of LCM for application in extreme drilling conditions in a loss circulation zone having vugs or large fractures (or both). For example, a zone with fractures larger than 10 mm or with vugs of diameter larger than 10 mm can lead to severe loss circulation. The apparatus 100 includes a drilling fluid reservoir 102 that can carry a wellbore drilling fluid, a spacer fluid reservoir 104 that can carry a spacer fluid, a LCM reservoir 106 that can carry a loss circulation material (LCM, specifically, the LCM to be evaluated) and a LCM test cell 108. The LCM test cell 108 includes a disk member 200 (FIG. 2A) that has multiple openings.

FIGS. 2A-2D are schematic diagrams of disk members, each with multiple openings. FIG. 2A shows the disk member 200 having a thickness T1 (for example, between 2 mm and 5 mm, for example, about 3 mm). The disk member 200 includes a circumferential sealing groove 204a, for example, a groove to hold an O-ring or similar seal. FIG. 2B shows a disk member 202 having a thickness T2 greater than the thickness of T1. For example, the thickness T2 can range between for example 15 mm to 50 mm (for example, about 20 mm or about 40 mm). Such disks can have two circumferential sealing grooves 204b and 204c axially separated from each other. FIG. 2C is a schematic diagram showing circular openings. Each opening is a through hole that extends from one axial end face of the disk member to another. FIG. 2D is a schematic diagram showing non-circular openings. The arrangement of the openings (circular or non-circular) on the end faces that is shown in FIGS. 2C and 2D are examples. Other arrangements are possible. For example, the openings need not be symmetrically formed. The non-circular openings can be oriented in different directions. A disk member (such as the disk member 200) together with the multiple openings represents a loss circulation zone in a subterranean zone in which a wellbore is drilled using the wellbore drilling fluid.

Each reservoir has an open volume in which the respective fluid can be carried. For example, the drilling fluid reservoir 102 can have a larger fluid-carrying volume compared to the LCM reservoir 106, which, in turn, can have a larger fluid-carrying volume compared to the spacer fluid reservoir 104. The LCM test cell can also have an open volume in which the LCM test material can be carried. The LCM test material includes a quantity of the LCM and a quantity of either the drilling fluid or the spacer fluid or both. The different fluid-carrying volumes can range between a few hundred milliliters (mL) and a few liters (L). In some implementations, each reservoir and the LCM test cell can have a substantially cylindrical fluid-carrying volume. A substantially cylindrical volume is a volume enclosed by a structure or surface that is cylindrical in shape within manufacturing tolerances. Other cross-sections are also possible.

Each reservoir and the LCM test cell can be constructed of a material that can withstand pressure (for example, greater than 500 psi and up to 3000 psi). For example, the material can be stainless steel. In general, the LCM test cell can be constructed of a material that is chemically resistant to the fluids flowed through the cell. For example, the LCM test cell material can be resistant to the corrosive effects of the fluids flowed through the cell.

The LCM test cell 108 is fluidically connected to the drilling fluid reservoir 102, the spacer fluid reservoir 104 and the LCM reservoir 106 using a fluid transfer network and a valve network. The fluid transfer network includes a first elongate tubular member 110a fluidically coupled to the LCM test cell 108. The valve network includes a first valve 112a in a flow path through the first elongate tubular member 110a. A second elongate tubular member 110b of the fluid transfer network fluidically couples the drilling fluid reservoir 102 to the first elongate tubular member 110b. A second valve 112b of the valve network in a flow path of the second elongate tubular member 110b controls flow of the wellbore drilling fluid from the drilling fluid reservoir 102 through the second elongate tubular member 110b and further to the first elongate tubular member 110a for flow to the LCM test cell 108. A third elongate tubular member 110c of the fluid transfer network fluidically couples the spacer fluid reservoir 104 to the first elongate tubular member 110a. A third valve 112c of the valve network in a flow path of the third elongate tubular member 110c controls flow of spacer fluid from the spacer fluid reservoir 104 through the third elongate tubular member 110c and further to the first elongate tubular member 110a for flow to the LCM test cell 108. A fourth elongate tubular member 110d of the fluid transfer network fluidically couples the LCM reservoir 106 to the first elongate tubular member 110c. A fourth valve 112d of the valve network in a flow path of the fourth elongate tubular member 110d controls flow of the LCM from the LCM reservoir 106 through the fourth elongate tubular member 110d and further to the first elongate tubular member 110a.

In some implementations, the apparatus 100 includes a first base member 114 supporting the drilling fluid reservoir 102, the LCM reservoir 106 and the spacer fluid reservoir 104. For example, the first base member 114 can be a substantially horizontal board or plate on which the three reservoirs are arranged adjacent to each other. A substantially horizontal board or plate is a board or plate that has a surface that is horizontal relative to the floor and within manufacturing tolerances. The apparatus 100 also includes a second base member 116 supporting the LCM test cell 108. For example, the second base member 116 is can be a substantially horizontal board or plate positioned vertically lower than the first base member 114 relative to a floor 118 on which the first base member 114 and the second base member 116 are positioned. The arrangement allows fluid transfer to the LCM test cell 108 using gravity and without the need for a pump. Alternatively, a pump can be used to apply pressure to flow the fluid through the LCM test cell 108. In such implementations, the first base member 114 and the second base member 116 can be at substantially the same elevation from the floor 118 or the first base member 114 can be nearer to the floor 118 than the second base member 116. A substantially same elevation means that difference in a distance from the floor 118 of the first base member 114 and a distance from the floor 118 of the second base member 116 is within a deviation of no more than 5%.

For example, the first base member 114 can include respective openings through which the drilling fluid reservoir 102, the spacer fluid reservoir 104 and the LCM reservoir 106 are passed. The reservoirs can be vertically positioned in the respective openings such that inlets to the reservoirs face upward (that is, away from the floor 118) and the outlets face downward (that is, towards the floor 118). Ends of the second, third and fourth elongate tubular members (110b, 110c and 110d, respectively) connect to the downward facing outlets of the drilling mud reservoir 102, the spacer fluid reservoir 104 and the LCM reservoir 106, respectively. Opposing ends of the second, third and fourth elongate tubular members (110b, 110c and 110d, respectively) connect to the circumferential surface of the first elongate tubular member 110a, which is substantially horizontal. One axial end of the first elongate tubular member 110a connects to an inlet to the LCM test cell 108. The other axial end of the first elongate tubular member 110a can be capped. Alternatively, one of the second, third or fourth elongate members (for example, the second elongate tubular member 110b) can connect to the other axial end instead of to the circumferential surface of the first elongate tubular member 110a.

The second base member 116 can also include an opening through which the LCM test cell 108 is passed. The LCM test cell 108 can be vertically positioned in the opening in the second base member 116 such that an outlet to the LCM test cell 108 faces downward (that is, towards the floor 118). The inlet to the LCM test cell 108 can be formed on a circumferential surface of the LCM test cell 108. Alternatively, the inlet can be formed on an axial end surface of the LCM test cell 108, the inlet facing vertically upward (that is, away from the floor 118). In such implementations, the first elongate tubular member 110a can include a vertical section that connects the substantially horizontal section of the member 110a to the upward-facing inlet of the LCM test cell 108.

The arrangement of the reservoirs and the test cell, and the elongate tubular members, as described earlier, can enable flowing components from the reservoirs, in a sequence, to the test cell such that the LCM to be tested is formed within the LCM test cell 108. The arrangement also enables flowing an acid to the LCM test cell 108 from one of the reservoirs (or from a different reservoir (not shown)) to determine if the LCM in the LCM test cell 108 can be dissolved. The arrangement additionally enables determining the effect of the spacer fluid on the LCM test and to pump contaminants into the LCM test cell 108 to study the tolerance of the LCM to contaminants.

The disk member 200 can be coupled to the LCM test cell 108, for example, inserted into the LCM test cell 108 from the bottom, and fastened. In this manner, the region of the LCM test cell 108 between the inlet and the outlet form a fluid flow path. Because the disk member 200 is positioned within the flow path, at least a portion of the LCM test material flowed into the LCM test cell 108 flows from the inlet through the multiple openings in the disk member 200 towards the outlet. The fluid transfer network includes a fifth elongate tubular member 110e attached to the outlet of the LCM test cell 108, and a fifth valve 112e in a flow path through the fifth elongate tubular member 110d. The portion of the LCM test material that flows through the multiple openings in the disk member 200 and out of the outlet of the LCM test cell 108 can flow through the fifth elongate tubular member 110e and can be collected by opening the fifth valve 112e.

Figure 3A:
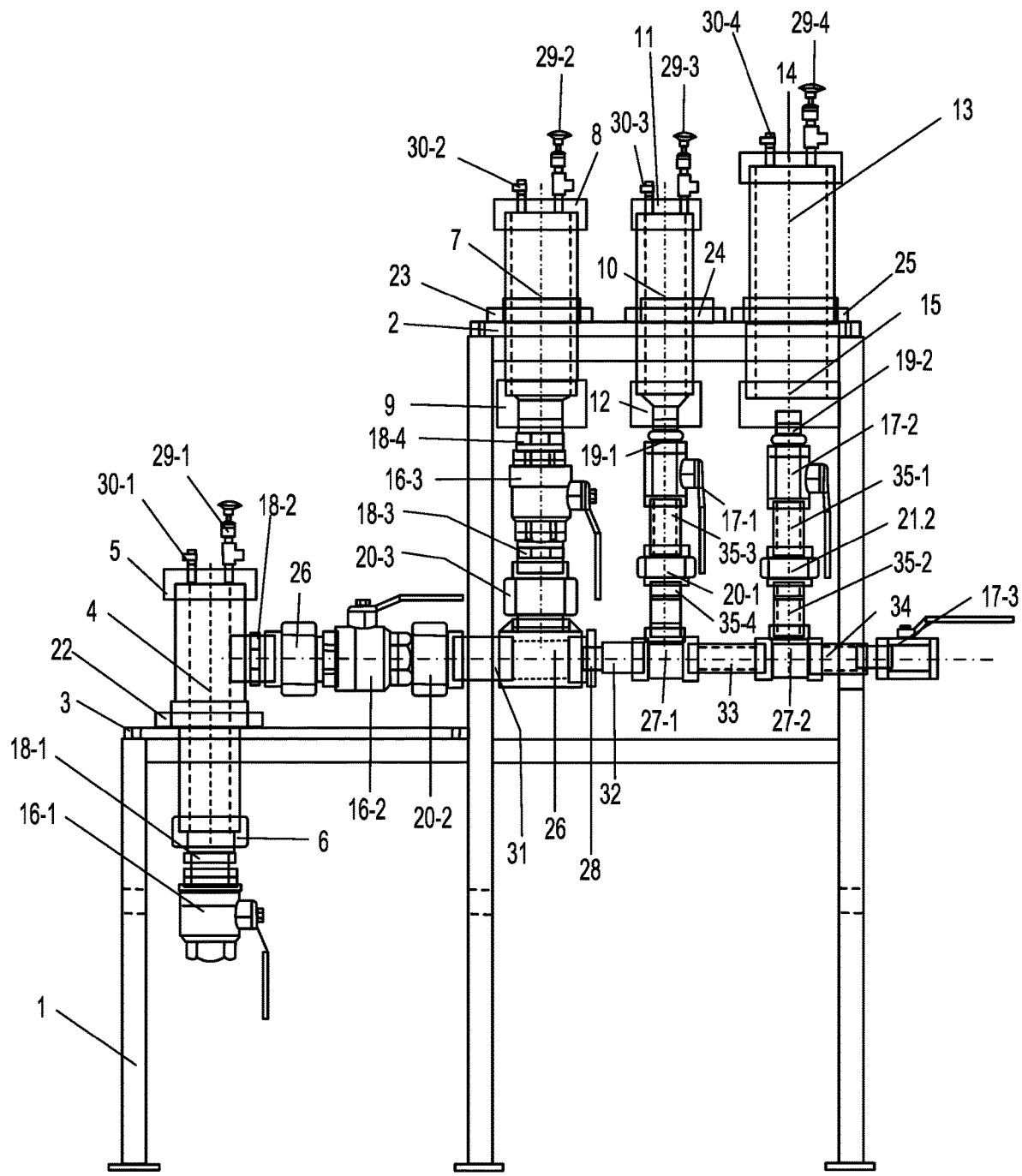
FIG. 3A is a schematic diagram of another example LCM test apparatus.
Figure 3B:
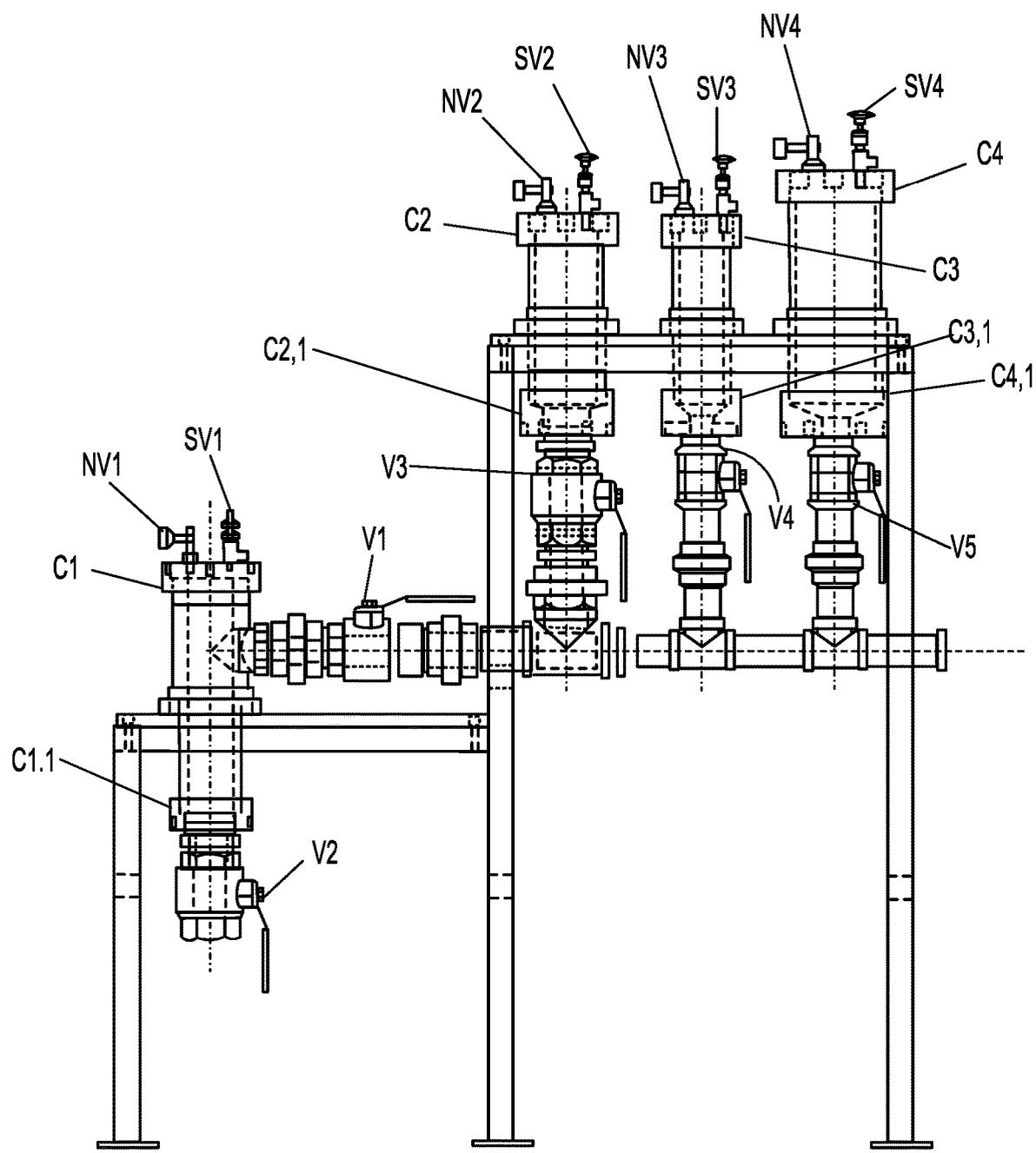
FIG. 3B is a schematic diagram of the example LCM test apparatus of FIG. 3A.

FIG. 3A is a schematic diagram of another example LCM test apparatus 300. FIG. 3B is a schematic diagram of the example LCM test apparatus 300 of FIG. 3A. In particular, FIG. 3B identifies the caps, needle valves and safety valves included in the valve network of the LCM test apparatus 300. The LCM test apparatus 300 is substantially similar to the LCM test apparatus 100 described earlier. Components of the LCM test apparatus 300 are shown in Table 1.

TABLE 1

List of parts

| # | Description | Quantity |
|---|---|---|
| 1 | Stand | 1 |
| 2 | Locating Plate 1 Top | 1 |
| 3 | Locating Plate 2 Middle | 1 |
| 4 | Main Test Cell 2 Liter | 1 |
| 5 | Main Test Top Cap | 1 |
| 6 | Main Test Bottom Cap | 1 |
| 7 | LCM Reservoir | 1 |
| 8 | LCM Top Cap | 1 |
| 9 | LCM Bottom Cap | 1 |
| 10 | Spacer Reservoir | 1 |
| 11 | Spacer Reservoir Top Cap | 1 |
| 12 | Spacer Reservoir Bottom Cap | 1 |
| 13 | Mud Reservoir | 1 |
| 14 | Mud Reservoir Top Cap | 1 |
| 15 | Mud Reservoir Bottom Cap | 1 |
| 16 | Ball Valve 1 | 3 |
| 17 | Ball Valve 2 | 3 |
| 18 | Nipple 1 | 4 |
| 19 | Nipple 2 | 2 |
| 20 | Union 1 | 3 |
| 21 | Union 2 | 2 |
| 22 | Main Test Cell adjusting Nut | 2 |
| 23 | LCM Reservoir Cell adjusting Nut | 2 |

TABLE 1-continued

List of parts

| # | Description | Quantity |
|---|---|---|
| 24 | Spacer Reservoir Cell adjusting Nut | 2 |
| 25 | Drilling Mud Reservoir Cell adjusting Nut | 2 |
| 26 | Tee 1 | 1 |
| 27 | Tee 2 | 2 |
| 28 | Reducer Connector | 1 |
| 29 | Safety Valve | 4 |
| 30 | Needle Valve | 4 |
| 31 | Union to Tee Connecting Pipe | 1 |
| 32 | Reducer Connector to Tee Connecting Pipe | 1 |
| 33 | Tee to Tee Connecting Pipe | 1 |
| 34 | Tee Ball Valve 2 Connecting Pipe | 1 |
| 35 | Ball Valve to Union Connecting Pipe | 4 |
| 36 | Allen Bolt | 8 (not labeled) |

The LCM is evaluated in main test cell 4 using various slotted and vugular metal disks (not shown in FIGS. 3A and 3B). For example, a sealing efficiency of the LCM is evaluated. The sealing efficiency is an ability of the LCM to prevent flow of a wellbore drilling fluid known as drilling mud through the multiple slots in the disks. A spacer fluid is sometimes used to prevent drilling mud-LCM contamination at the interface. Plugging and sealing efficiency are used to represent the same parameter. The main test cell 4 has threaded type top cap C1 and bottom cap C1.1. Pressure inlet/outlet needle valve NV1 and safe valve SV1 are fixed on the top cap C1. Ball valve V2 is attached with the bottom cap C1.1, which is the outlet of the main test cell 4. The LCM test apparatus 300 includes three reservoirs, namely, the LCM reservoir 7, the spacer fluid reservoir 10 and the mud reservoir 13. These reservoirs have respective threaded top caps (C2, C3 and C4), and bottom caps (C2.1, C3.1 and C4.1). The top caps of the reservoir chambers are fixed with respective pressure inlet/outlet needle valves (NV2, NV3 and NV4) and safe valves (SV2, SV3 and SV4). The bottom cap of the reservoir chambers are fixed with respective ball valves (V3, V4 and V5), which are connected to union. The other end of the unions of the three reservoirs are connected to Tee joints, which connect a pipe to main test cell 4 through a ball valve V1. A valve is fixed on the other end of the pipe. The entire assembly is supported by a stand (for example, a metal stand) and can be mounted on the floor. The main test cell 1 and the three reservoir chambers are interconnected through various ball valves and can be disconnected by removing the unions connecting the different parts. The ability to interconnect and disconnect the different components facilitates cleaning the test apparatus.

In operation, nitrogen is flowed into each pressure inlet needle valve (NV1, NV2, NV3 and NV4) to flow the fluids from the reservoirs into the main test cell 4. The nitrogen applies a downward pressure on the fluid forcing the fluid toward the slotted disk. An ideal LCM will not permit any fluid to flow through the slots in the disk. In practice, a discharge of less than or equal to substantially 30 milliliters (ml) (give or take about 5 ml) indicates an acceptable sealing efficiency for the LCM. In some instances, a reduction of 20-25% in the loss of the drilling fluid also indicates an acceptable sealing efficiency for the LCM. In some implementations, the nitrogen pressure can be applied to the pressure inlet needle valve of the main test cell 14 (NV4) after the fluids from the other reservoirs have been flowed into the cell 4.

Figure 4:
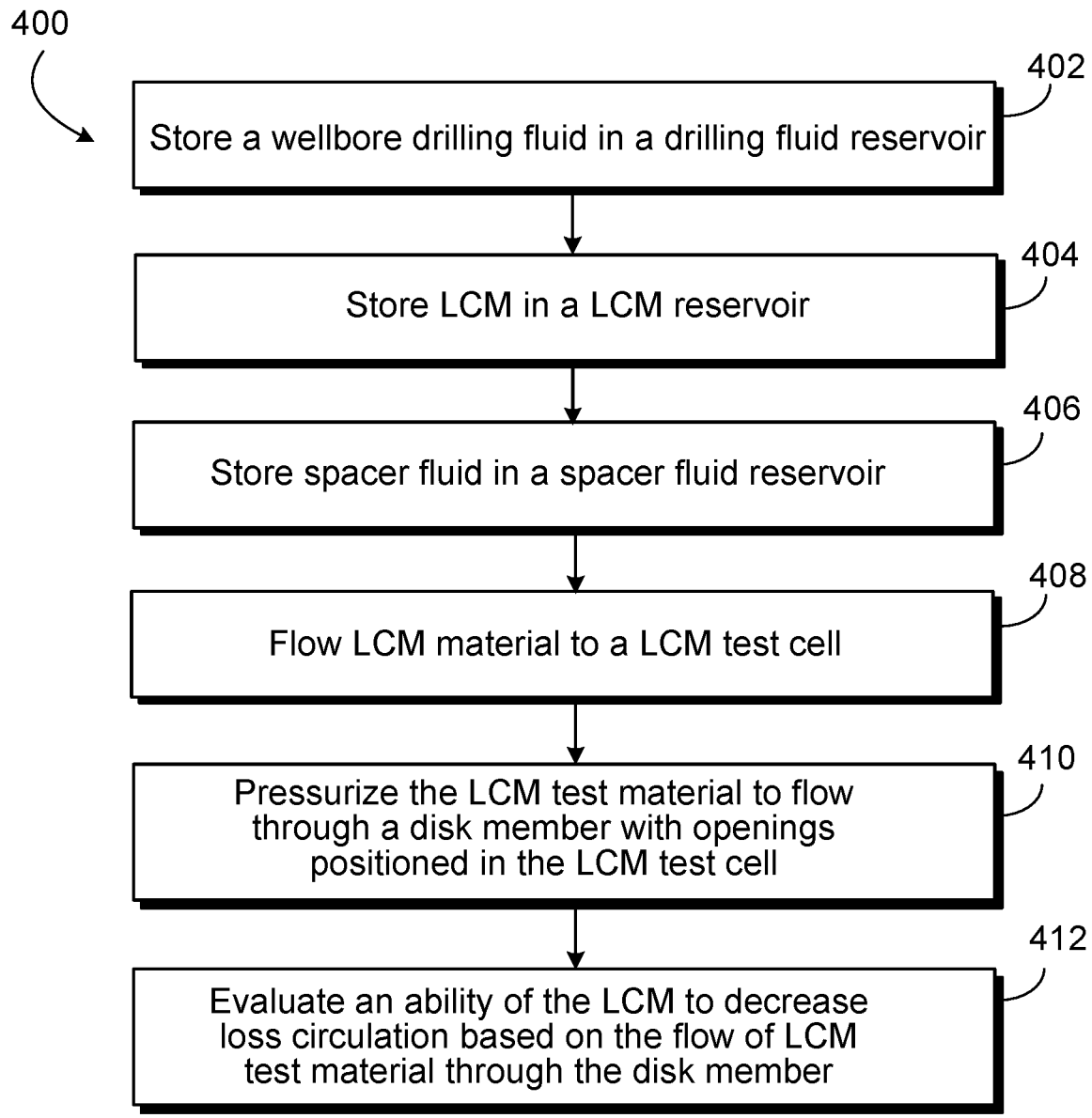
FIG. 4 is a flowchart of an example of a process for evaluating LCM using the example LCM test apparatus of FIGS. 3A and 3B.

FIG. 4 is a flowchart of an example of a process 400 for evaluating LCM using the example LCM test apparatus 300. The process can be performed by an operator of the LCM test apparatus. The process can be performed in a laboratory or under laboratory conditions. Before starting a test, all valves can be closed and all regulators can be rotated fully. All seals (for example, O-rings or similar seals) can be checked and replaced if necessary. A thin coat of grease (for example, silicone grease) can be applied around the seals and the cell caps. O-ring recesses can be checked for cleanliness and an O-ring can be inserted inside the cell recess on an axial end of the LCM test cell. A disk member with multiple openings can be selected and inserted into the LCM test cell, for example, from the bottom. As described earlier, the disk member with the multiple openings can be selected based on the loss circulation zone to be simulated using the LCM test cell. For example, to simulate a severe loss zone, a disk member in which the multiple openings have a dimension of at least 40 mm (for example, 50 mm) can be selected. To simulate moderate or seepage type loss circulation zones, a disk member with comparatively smaller openings can be selected. The bottom cap of the LCM test cell can then be fastened to the disk member. The top cap of the LCM test cell can then be fastened to the test cell body. Similarly, the respective caps of the drilling fluid reservoir, the LCM reservoir and the spacer fluid reservoir can be fastened to the respective reservoirs.

Subsequently, pre-setup for the pressure safety valve for each reservoir can be started individually. To do so, all caps and valve connected to the reservoirs can be completely closed. The spring that covers the desired set pressure can be selected, installed and adjusted to the maximum. For example, a first spring can be selected for a pressure range of 350 psi to 750 psi. A second spring can be selected for a pressure range of 1500 psi to 2250 psi. Pressure can be applied to the chamber until the required pressure is reached. The inlet valve can be closed. The safety valve can be opened until the pressure inside the chamber is released. The position of the safety valve cap can be locked.

At 402, LCM can be stored in (for example, poured into) a LCM reservoir. The LCM reservoir can be sealed using the corresponding top and bottom caps. To do so, cap C2 can be opened and the LCM placed inside the fluid-carrying volume in the LCM reservoir. Cap C2 can then be closed. At 404, a wellbore drilling fluid can be stored in (for example, poured into) a drilling fluid reservoir. At 406, spacer fluid can be stored in a spacer fluid reservoir. The respective fluids can be stored in the respective reservoirs by implementing techniques similar to step 402.

At 408, LCM can be flowed to the LCM test cell. In some implementations, a quantity of each of the LCM, the drilling fluid or the spacer fluid can be metered. In addition, the fluids can be flowed to the LCM test cell in a desired sequence, for example, LCM, spacer fluid, drilling fluid, or similar sequence. To flow the LCM to the LCM test cell, pressure can be applied for a duration (for example, two minutes or different duration) through NV2. After the duration and if sufficient LCM has been flowed to the LCM test cell, the application of pressure can be stopped and the cap C1 and the valves V1 and V3 can be closed. Similar procedure can be adopted to flow the drilling fluid or the spacer fluid (or both) using the respective caps and valves.

At 410, the LCM test material, which includes the LCM and either the drilling fluid or the spacer fluid or both, can be pressurized to flow through the disk member positioned in the LCM test cell. To do so, for example, valve V2 can be opened and a collection vessel can be positioned at the outlet of the LCM test cell. Pressure can be applied in increments (for example, in 50 psi or greater or smaller increments)

until a desired test pressure is reached. The valve NV1 can be closed and the pressure in the LCM test cell left undisturbed for a duration (for example, 30 minutes or greater or smaller duration). If rapid discharge of LCM test material in bulk volume is observed through the outlet of the LCM test cell, the application of pressure can be ceased. Otherwise, the quantity of the LCM test material discharged through the outlet can be collected and recorded.

At 412, an ability of the LCM to decrease loss circulation can be evaluated based on the flow of LCM test material through the disk member. The LCM that permits no fluid discharge or the least fluid discharge through the outlet of the LCM cell is the most effective LCM. Different LCM samples can be prepared by varying (for example, increasing) the concentration of the LCM in the drilling fluid or the combination of the drilling fluid and the spacer fluid. Each LCM sample can be evaluated at different pressures applied to the LCM test cell. Each LCM sample can additionally be evaluated using different slotted disks, each having openings of different sizes. In experiments in which the LCM is made from two components, the concentration of the activator that is used to form the LCM can be varied.

After the test, all the pressure lines from needle valves NV1, NV2, NV3 and NV4 are disconnected. The pressure inside the cells is released by opening needle valves NV1, NV2, NV3 and NV4. In case of trapped pressure inside the LCM test cell, pressure is first relieved through needle valve NV1. If insufficient pressure is relieved, safety valve SV1 is used for reducing the pressure. To further release the pressure, the union for valve V1 is released slowly so that the trapped pressure can escape from the main test cell. Prior to the next test, the test cells, cell caps and all fittings can be cleaned thoroughly. All threads can be cleaned and any debris removed. All fittings can be further cleaned, for example, by blowing air. All O-rings can be lubricated to ensure proper fit and increased life. The threads can be periodically inspected for damage or wear, and replaced as necessary.

By implementing the techniques described here, the effectiveness of LCM in loss circulation zones having aperture sizes greater than 40 mm (for example, up to 50 mm) can be determined. Thus, particular implementations of the subject matter have been described. Other implementations are within the scope of the following claims.

What is claimed is:

1. A loss circulation material (LCM) testing apparatus comprising:
    a drilling fluid reservoir configured to carry a wellbore drilling fluid;
    a LCM reservoir configured to carry a loss circulation material (LCM);
    a spacer fluid reservoir configured to carry a spacer fluid; and
    a LCM test cell comprising a disk member comprising a plurality of openings, the disk member representing a loss circulation zone in a subterranean zone in which a wellbore is drilled using the wellbore drilling fluid, the LCM test cell fluidically connected to the drilling fluid reservoir, the LCM reservoir and the spacer fluid reservoir, the LCM test cell configured to fluidically receive a quantity of LCM from the LCM reservoir and to evaluate a sealing efficiency of the LCM, the sealing efficiency being an ability of the LCM to prevent flow of the wellbore drilling fluid through the plurality of openings in the disk member.

2. The apparatus of claim 1, wherein each of the drilling fluid reservoir, the LCM reservoir, the spacer fluid reservoir and the LCM test cell comprises a respective nitrogen pressure inlet configured to receive nitrogen and to transfer the received nitrogen to the LCM test cell to apply a pressure on a mixture of the wellbore drilling fluid and the spacer fluid comprising the quantity of the LCM to evaluate the ability of the LCM to prevent flow of the wellbore drilling fluid through the plurality of openings in the disk member.

3. The apparatus of claim 1, further comprising a fluid transfer network comprising:
    a first elongate tubular member fluidically coupled to the LCM test cell;
    a second elongate tubular member fluidically coupled to the drilling fluid reservoir and to the first elongate tubular member;
    a third elongate tubular member fluidically coupled to the LCM reservoir and to first elongate tubular member; and
    a fourth elongate tubular member fluidically coupled to the spacer fluid reservoir and to the first elongate tubular member, the fluid transfer network configured to flow at least one the wellbore drilling fluid, the LCM or the spacer fluid to the LCM test cell.

4. The apparatus of claim 1, further comprising a valve network comprising:
    a first valve in a flow path through the first elongate tubular member;
    a second valve in a flow path through the second elongate tubular member;
    a third valve in a flow path through the third elongate tubular member; and
    a fourth valve in a flow path through the fourth elongate tubular member, wherein the valve network is configured to selectively flow at least one the wellbore drilling fluid, the LCM or the spacer fluid to the LCM test cell.

5. The apparatus of claim 1, further comprising:
    a first base member supporting the drilling fluid reservoir, the LCM reservoir and the spacer fluid reservoir; and
    a second base member supporting the LCM test cell, the second base member positioned vertically lower than the first base member relative to a floor on which the first base member and the second base member are positioned.

6. The apparatus of claim 1, wherein the LCM test cell comprises:
    an inlet fluidically connected to the first elongate tubular member; and
    an outlet, wherein a LCM test cell region between the inlet and the outlet defining a fluid flow path, wherein the disk member is positioned within the flow path such that fluid flowed from the inlet to the outlet at least partially flows through the disk member.

7. The apparatus of claim 1, wherein the LCM test cell is configured to be pressurized up to 2000 pounds per square inch (psi).

8. The apparatus of claim 1, wherein each of the drilling fluid reservoir, the spacer fluid reservoir and the LCM reservoir is configured to be pressurized up to 500 psi.

9. The apparatus of claim 1, wherein the disk member comprising the plurality of openings is a first disk member comprising a first plurality of openings, wherein each of the first plurality of openings are substantially up to 40 mm in size.

10. The apparatus of claim 1, further comprising a plurality of disk members, each comprising a respective plurality of openings, the plurality of disk members including the first disk member, and further comprising a second disk member comprising a second plurality of openings, wherein the second plurality of openings range between substantially 5 mm and up to 40 mm in size.

11. A method of evaluating a loss circulation material (LCM) comprising:
storing a wellbore drilling fluid in a drilling fluid reservoir;
storing LCM in a LCM reservoir;
storing spacer fluid in a spacer fluid reservoir;
flowing LCM test material to a LCM test cell fluidically coupled to the drilling fluid reservoir, the LCM reservoir and the spacer fluid reservoir, the LCM test material comprising a quantity of LCM from the LCM reservoir;
pressurizing the LCM test material to flow through a disk member comprising a plurality of openings, the disk member positioned within the LCM test cell, the disk member representing a loss circulation zone in a subterranean zone in which a wellbore is drilled using the wellbore drilling fluid; and
determining a sealing efficiency of the LCM, the sealing efficiency being an ability of the LCM to prevent flow of the wellbore drilling fluid through the plurality of openings in the disk member.

12. The method of claim 11, wherein flowing the LCM test material to the LCM test cell comprises:
positioning the drilling fluid reservoir, the LCM reservoir and the spacer fluid reservoir on a first base member; and
positioning the LCM test cell on a second base member positioned vertically lower than the first base member relative to a floor on which the first base member and the second base member are positioned, wherein the LCM test material flows to the LCM test cell under gravity.

13. The method of claim 11, further comprising selectively controlling a first quantity of the drilling fluid or a second quantity of the spacer fluid or a third quantity of the LCM flowed to the LCM test cell using a fluid transfer network that fluidically couples the drilling fluid reservoir, the spacer fluid reservoir and the LCM reservoir, and a valve network that controls flow of the drilling fluid, the spacer fluid and the LCM to the LCM test cell.

14. The method of claim 11, wherein the LCM test material is pressurized to flow through the disk member at a pressure of substantially 2000 psi.

15. The method of claim 11, the LCM test material is flowed to the LCM test cell at a pressure of substantially 500 psi.

16. The method of claim 11, wherein pressurizing the LCM test material to flow through the disk member comprising the plurality of openings comprises:
sealing the disk member to the LCM test cell between an inlet to the LCM test cell and an outlet to the LCM test cell; and
measuring a quantity of the LCM test material that flows from the inlet through the disk member through the outlet within a certain duration.

17. The method of claim 16, wherein pressurizing the LCM test material comprises applying a nitrogen pressure to pressurize the LCM test cell to flow the LCM test material toward the disk member.

* * * * *

UNITED STATES PATENT AND TRADEMARK OFFICE
CERTIFICATE OF CORRECTION

PATENT NO. : 11,111,742 B2
APPLICATION NO. : 15/879783
DATED : September 7, 2021
INVENTOR(S) : Amanullah et al.

Page 1 of 1

It is certified that error appears in the above-identified patent and that said Letters Patent is hereby corrected as shown below:

In the Claims

<u>Column 12</u>
Claim 3, Line 21, after "one" insert -- of --;
Claim 4, Line 33, after "one" insert -- of --.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*